Figure 1:
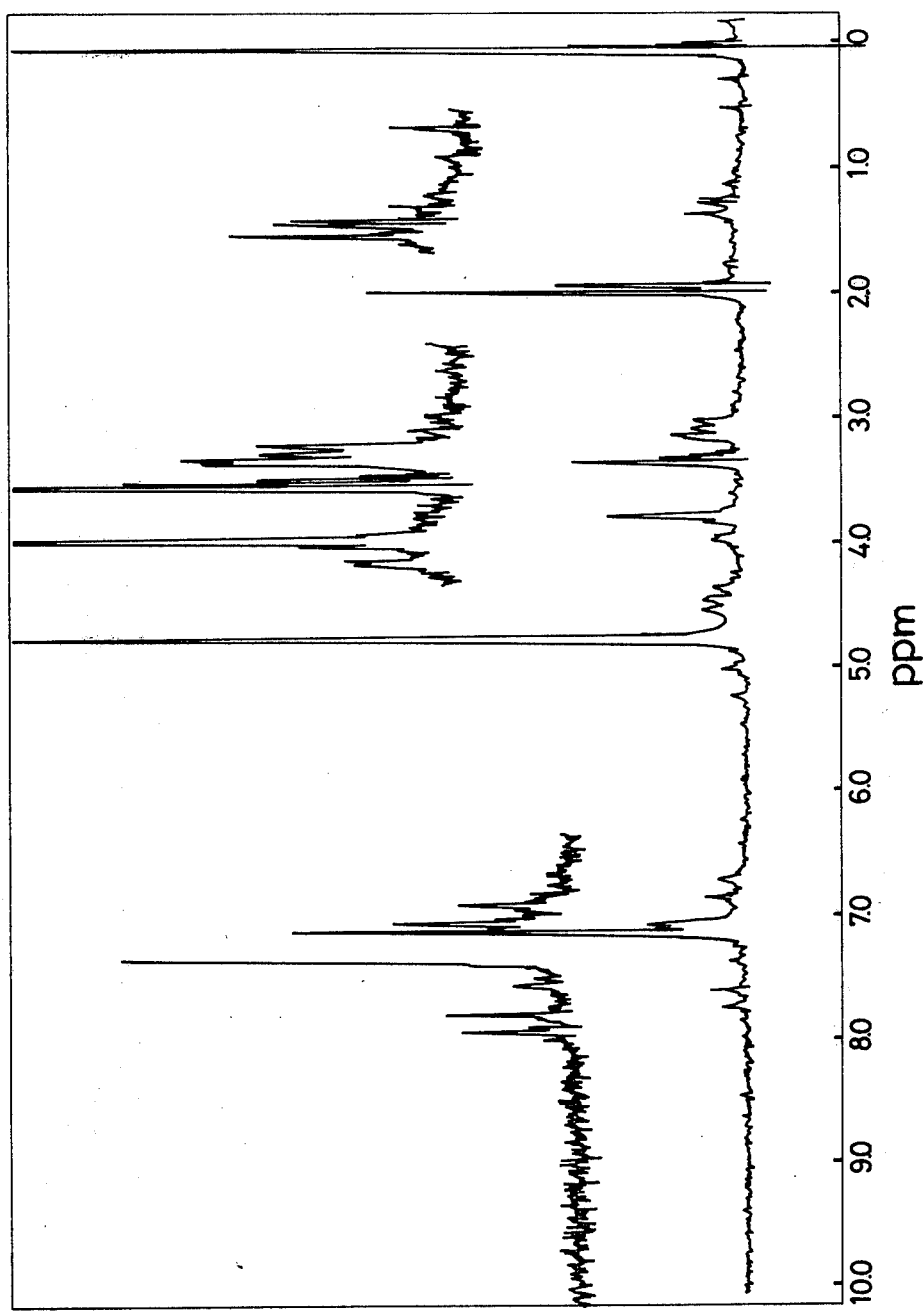

United States Patent

Sugiyama et al.

[11] 4,432,896
[45] Feb. 21, 1984

[54] DERIVATIVES OF HIPPURYL-L-PHENYLALANINE

[75] Inventors: Masami Sugiyama, Hachioji; Yasushi Kasahara, Tama; Yoshihiro Ashihara, Fuchu, all of Japan

[73] Assignee: Fujirebio Kabushiki Kaisha, Tokyo, Japan

[21] Appl. No.: 423,494

[22] Filed: Sep. 24, 1982

[30] Foreign Application Priority Data

Dec. 16, 1981 [JP] Japan .................................. 56-201587

[51] Int. Cl.³ .......................................... C07C 103/52
[52] U.S. Cl. ................................ 260/112.5 R; 435/23; 435/24
[58] Field of Search ................... 260/112.5 R; 562/444

[56] References Cited

PUBLICATIONS

Krainova et al., Zhurnal Obshchei Khimii, vol. 39, No. 1, pp. 92–96, 1969.

Lange et al., Biochemistry, vol. 13, No. 9, 1974, pp. 1983–1986.

Davies et al., Biochemistry, vol. 7, No. 3, 1968, pp. 1090–1099.

*Primary Examiner*—Natalie Trousof
*Assistant Examiner*—Deborah A. Dalton
*Attorney, Agent, or Firm*—Flynn, Thiel, Boutell & Tanis

[57] ABSTRACT

Derivatives of hippuryl-L-phenylalanine having the following general formula:

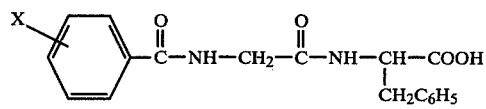

wherein X represents OH or $CH_3O$ useful as substrates for measuring the actively of carboxy peptidose A.

4 Claims, 2 Drawing Figures

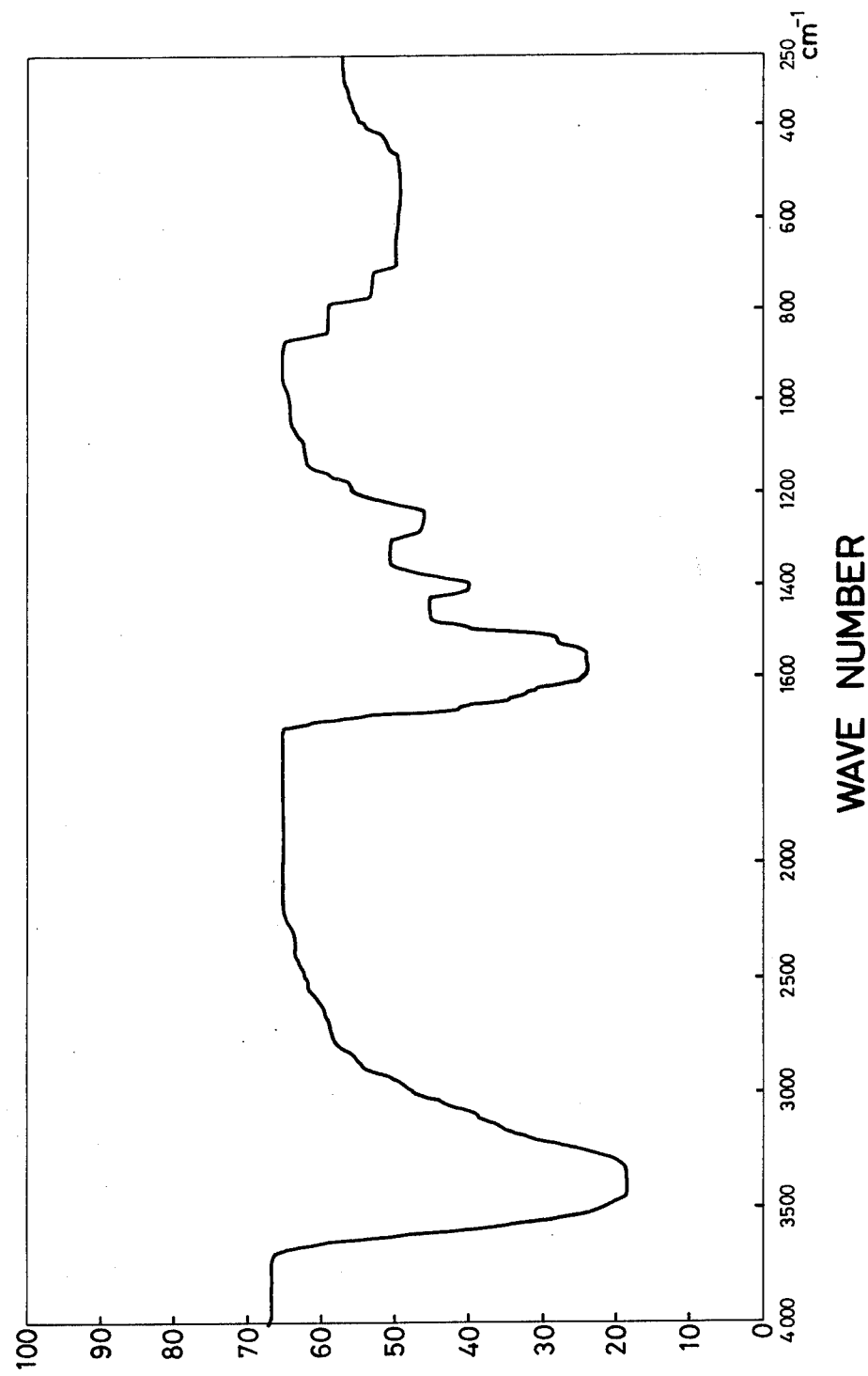

DERIVATIVES OF HIPPURYL-L-PHENYLALANINE

EXPLANATION OF THE INVENTION

The present invention relates to derivatives of hippuryl-L-phenylalanine having the following general formula:

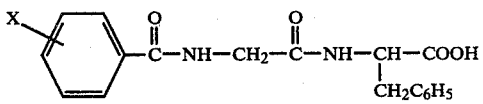

wherein X represents OH or $CH_3O$.

Derivatives of hippuryl-L-phenylalanine of the present invention are used as a substrate for measuring the activity of carboxypeptidase A (hereinafter referred to as CP-A for short).

The CP-A is a protein-decomposing enzyme which is found in the pancreas and the blood serum. The activity of the CP-A depends on diseases. Accordingly, by measuring the activity of the CP-A, the extent of the diseases can be detected.

The activity of the CP-A can be measured by using X-hippuryl-L-phenylalanine of the present invention as follows:

X-hippuryl-L-phenylalanine is added to a liquid containing the CP-A, such as human blood serum or humor, to produce X-hippuric acid and L-phenylalanine by decomposing x-hippuryl-L-phenylalanine by the CP-A. Hippuricase is added to the liquid to produce X-benzoic acid and glycine by decomposing X-hippuric acid. Quinonimine dye is produced by the reaction of X-benzoic acid with 4-aminoantipyrine in the presence of an oxidizing agent. The concentration of the quinonimine dye is colorimetrically measured to indicate the activity of the CP-A.

Derivatives of hippuryl-L-phenylalanine can be prepared by the way as shown below:

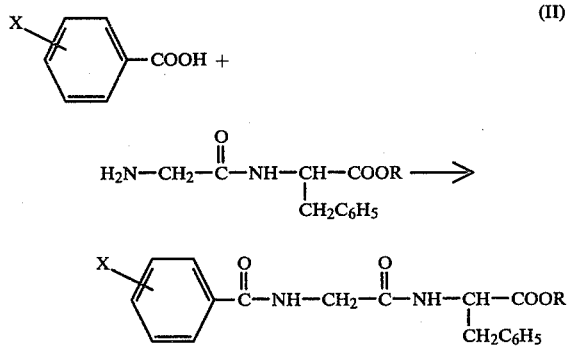

wherein X represents OH or $CH_3O$, and R represents alkyl group.

This reaction is carried out in an organic solvent such as dicyclohexylcarbodiimide, and the compound having Formula (I) can be obtained by hydrolysis of the compound having Formula (II).

Process of preparing the compounds of the present invention will be shown below:

1. Synthesis of p-hydroxyhippuryl-L-phenylalanine:
20.9 g (0.1 M) of carbobenzoxyglycine was dissolved in 500 ml of dichloromethane and to this solution was added 19.3 g (0.1 M) of L-phenylalanine ethyl ester, and to this mixture cooled in ice-water of 0° C. was added 20.6 g (0.1 M) of dicyclohexylcarbodiimide, and then this mixture was stirred overnight.

The deposit was filtered off by a glass filter, and after the filtrate was washed with a 0.1% aqueous solution of $NaHCO_3$ three times and then washed with a 0.1 N aqueous solution of HCl three times, it was dried over anhydrous magnesium sulfate and freed of dichloromethane under reduced pressure to obtain carbobenzoxyglycyl-L-phenylalanine ethyl ester, and to this ester was added 250 ml of HBr-saturated acetic acid, and after the mixture was stirred for 30 minutes, anhydrous ether was added to the mixture to produce a precipitate. The filtered off precipitate was washed with ether to obtain glycyl-L-phenylalanine ethyl ester.HBr.

16.5 g (0.05M) of glycyl-L-phenylalanine ethyl ester.HBr, 9.0 g (0.05 M) of p-acetoxybenzoic acid and 7.5 ml (0.05 M) of triethylamine were dissolved in 250 ml of dichloromethane, and after this solution was cooled to 0° and there was added 10.3 g (0.05 M) of dicyclohexylcarbodiimide, this mixture was stirred for 24 hours. The precipitate produced was removed, and after the filtrate was washed with a 0.1% aqueous solution of $NaHCO_3$ and then with a 0.1 N aqueous solution of HCl, and it was dried over anhydrous magnesium sulfate, dichloromethane was distilled off under reduced pressure to obtain p-acetoxyhippuryl-L-phenylalanine ethyl ester.

7.96 g (0.02 M) of p-acetoxyhippuryl-L-phenylalanine ethyl ester was dissolved in 50 m of methanol, and to this solution was added 70 ml of a 0.1 N aqueous solution of NaOH. After the solution was stirred at room temperature for one hour, the pH of the solution was adjusted to 7 by adding HCl, and after the solution was distilled under reduced pressure to remove the solvent, methanol was added to the residue. Insoluble matter was filtered off, and to the filtrate was added ethanol to produce a precipitate. The filtered off precipitate is p-hydroxyhippuryl-L-phenylalanine, which was obtained in an amount of 4.01 g. m.p. 163°–167.5° C. (decomposed)

FIG. 1 shows 'H-nmr absorption spectrum of p-hydroxyhippuryl-L-phenylalanine, and FIG. 2 shows infrared absorption spectrum thereof.

2. Synthesis of o-hydroxyhippuryl-L-phenylalanine:

Glycyl-L-phenylalanine ethyl ester.HBr was obtained by using carbobenzoxyglycine as a starting material and repeating Procedure 1 supra.

16.5 g (0.05 M) of glycyl-L-phenylalanine ethyl ester.HBr, 9.0 g (0.05 M) of o-acetoxybenzoic acid and 7.5 ml (0.05 M) of triethylamine were dissolved in 250 ml of dichloromethane, and after this solution was cooled to 0° C. and there was added 10.3 g (0.05 M) of dicyclohexylcarbodiimide, this mixture was stirred for 24 hours. The precipitate produced was removed, and after the filtrate was washed with a 0.1% aqueous solution of $NaHCO_3$ and then with a 0.1 N aqueous solution of HCl, and it was dried over anhydrous magnesium sulfate, dichloromethane was distilled off under reduced pressure to obtain o-acetoxyhippuryl-L-phenylalanine ethyl ester.

7.69 g (0.02 M) of o-acetoxyhippuryl-L-phenylalanine ethyl ester was dissolved in 50 ml of methanol and to this solution was added 70 ml of a 0.1 N aqueous solution of NaOH, and then this solution was treated by repeating the same procedure as Procedure 1 supra to obtain o-hydroxyhippuryl-L-phenylalanine.

3. Synthesis of p-methoxyhippuryl-L-phenylalanine:

p-methoxyhippuryl-L-phenylalanine was able to be obtained by repeating the same procedure as Procedure 1 supra, except that 7.4 g (0.05 M) of p-methoxybenzoic acid was used instead of 9.0 g (0.05 M) of p-acethoxybenzoic acid.

We claim:

1. Derivatives of hippuryl-L-phenylalanine having the following general formula:

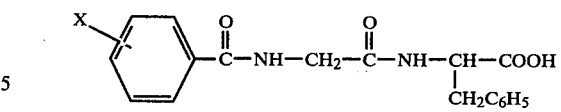

wherein X represents OH or CH₃O.

2. P-hydroxyhippuryl-L-phenylalanine.
3. o-hydroxyhippuryl-L-phenylalanine.
4. p-methoxyhippuryl-L-phenylalanine.